United States Patent [19]
Harnoncourt

[11] Patent Number: 5,419,326
[45] Date of Patent: May 30, 1995

[54] SPIROMETER, MORE PARTICULARLY AN ULTRASONIC SPIROMETER

[75] Inventor: Karl Harnoncourt, Graz, Austria

[73] Assignee: NDD Medizintechnik GmbH, Estenfeld, Germany

[21] Appl. No.: 190,053

[22] PCT Filed: May 6, 1993

[86] PCT No.: PCT/EP93/01109
 § 371 Date: Jan. 31, 1994
 § 102(e) Date: Jan. 31, 1994

[87] PCT Pub. No.: WO93/24810
 PCT Pub. Date: Dec. 9, 1993

[30] Foreign Application Priority Data
 Jun. 3, 1992 [DE] Germany .................. 42 18 317.0
 Jul. 7, 1992 [DE] Germany .................. 42 22 286.9

[51] Int. Cl.⁶ .................................................. A61B 8/00
[52] U.S. Cl. .............................. 128/660.02; 73/861.28; 128/719
[58] Field of Search ............... 128/660.01, 660.02, 128/660.03, 661.07, 719, 718, 725, 716, 730; 72/86.28, 861.03, 597

[56] References Cited
U.S. PATENT DOCUMENTS 3,738,169 6/1973 Courty .......................... 73/861.03
3,901,078 8/1975 McShane ..................... 73/861.03
5,035,147 7/1991 Woodward .................. 73/861.28

Primary Examiner—George Manuel

[57] ABSTRACT

The invention relates to a spirometer, more particularly an ultrasonic spirometer, in the case of which a pair of cells, of which one is a transmitter cell and the other is a receiver cell, are arranged in a test section with an oblique or perpendicular alignment to the axis of the duct containing the test section. For this purpose in accordance with the invention a readily replaced duct, which if necessary is sterile, is inserted into the test duct. In order to design such an ultrasonic spirometer so that it may be employed for clinical purposes, it is necessary for it to be kept sterile in a simple fashion. For this purpose in accordance with the invention a sterile duct in inserted into the test duct with an accurate fit and at the transition between it and the test section it has test windows such that inserts are inserted into corresponding openings which are transparent for acoustic waves but substantially impermeable for microorganisms and dirt.

9 Claims, 1 Drawing Sheet

SPIROMETER, MORE PARTICULARLY AN ULTRASONIC SPIROMETER

The invention relates to a spirometer, more particularly an ultrasonic spirometer, in the case of which a pair of cells, of which one is a transmitter cell and the other is a receiver cell, are arranged in a test section with an oblique or perpendicular alignment to the axis of the test duct.

Spirometry, that is to say the measurement of air movements in the course of breathing, is generally performed using measuring instruments which measure the volumetric flow of a gas in a duct by determining the velocity of flow. The volumetric flow may be found as the product of the cross section of the duct and the mean velocity of flow. In the case of the use of a measuring instrument for the investigation of the performance of the human lung the variations in the volumetric flow with time during breathing in and out are of interest. By integration it is possible to determine the quantity of air breathed in or out in a certain period of time. Presently various methods of flow measurement are employed in pulmonary function diagnostics (pneumotachography). There are methods such as measurement of back pressures upstream from a constant resistance (for example woven metal fabric) or using Fleisch pneumotachographs, measurement using a propeller, measurement using a thermistor and other methods.

The patent publications JP 60-117149 A and CH 669463 A5 disclose so-called ultrasonic spirometers of the type initially mentioned, in the case of which a transmitter cell and a receiver cell are arranged in a test section with an oblique or perpendicular alignment to the axis of the test duct. In these known ultrasonic spirometers the flow velocity is determined using ultrasonic doppler measurement. This measuring technique renders possible an accurate determination of the flow field on the axis of the test duct section and consequently an exact determination of the volumetric flow. In the case of spirometry such measuring instruments do however suffer from the disadvantage the test duct section may be contaminated with microorganisms and the like. Therefore it is necessary for the tube to be disinfected after each measurement, something which is on the one hand expensive and on the other hand represents a continual danger of infection if it is not performed properly.

One solution to this hygienic problem has been attempted by the development of so-called disposable sensors. Accordingly attempts have already been made to provide the test duct through question the respiratory gas flows with a nozzle-like restriction with a tube joining it at its narrowest point to provide a connection for the measuring device. This duct with the nozzle-like restriction, which is contaminated with respiratory air is now to be designed as a disposable item, which can be replaced after being employed once. This solution, which is valuable from the point of hygiene, does however lead to the danger of interference with the flow to be measured and for this reason spurious readings.

One object of the present invention is to provide such a further development of the spirometer of type described that measurement of the flow velocity free of interference while ensuring the required hygienic precautions is rendered possible.

Taking as a starting point a spirometer of the type initially mentioned this object is to be attained by the characterizing features of claim 1. Accordingly a readily replaced and if necessary sterile tube is inserted into the test duct of the ultrasonic spirometer with an accurate fit. At the transition with the test section the replaceable tube possesses windows of that type in which inserts are placed, which on the one hand allow the passage of sound waves but on the other hand are substantially impermeable to germs. This design is based on the thought that in the part in which the test section opens towards the axis of the test duct, windows are present which allow the passage of ultrasonic vibrations, since the wall surface of an inserted lining duct would excessively damp the ultrasonic waves and consequently would render any ultrasonic doppler measurement impossible. On the other hand owing to the inserts within the measuring windows it is possible to ensure that as far as possible no germs and furthermore as far as possible no foreign matter of any other type is able to find its way into the test section, something which again would otherwise call for time-consuming and complex cleaning of the measuring.

In accordance with a further advantageous development of the invention the inserts consist of elastic plastic, more particularly foam rubber. Experimental investigations have shown that the elasticity of foam rubber allows transmission of the ultrasonic waves through the test window. On the other hand the test windows shut off by the foam rubber insert are essentially impermeable to microorganisms contained in the respiratory air. The pores of the foam rubber permit a labyrinth-like, open form of communication and hence do not constitute a closure, as for instance is the case with a sealing membrane. In use there is no flow through the pores, since the sensor, which is arranged behind the foam rubber window, is arranged in blind hole. In this respect the inserts of elastic plastic and more particularly of foam rubber may be impregnated with a disinfectant.

In order to be able to provide the test windows exactly in the desired positions in the spirometer, the latter may be so divided in a plane extending through the test duct that it may folded open along this plane extending the duct. After the spirometer has been so folded into the open position it is then possible for the sterile lining duct, once it has been taken out of its package, to be arranged in exactly the right position. For this purpose it is possible, if necessary, to provide locating spurs or locating flanges on the test duct, which additionally serve to prevent an slipping out of the correct position of the duct when the ultrasonic spirometer is folded into the closed position.

In keeping with yet another possible form of the invention the inserts consist of extremely thin plates. They have to be so thin in comparison with the wavelengths produced that they may be caused to vibrate by the ultrasonic waves. For this purpose it is possible to utilize films of Mylar. In this case the plates are transparent for the ultrasonic waves. The sterile duct then may possess two oppositely placed parallel surfaces, whose width is ideally the same the width of the plates which in shape are rectangular. The rectangular plates constituting the inserts and having a rectangular form are co-planar with the corresponding parallel surfaces.

In order to ensure correct positioning of the two possible surfaces in relation to the test window, the sterile tube may for its part have locating means ensuring insertion in the correct position. Such locating means may for example consist of a flange with a locating recess.

Further advantageous developments and convenient forms of the invention will be understood from the following detailed descriptive disclosure of embodiments thereof in conjunction with the accompanying drawings.

Figure 1:
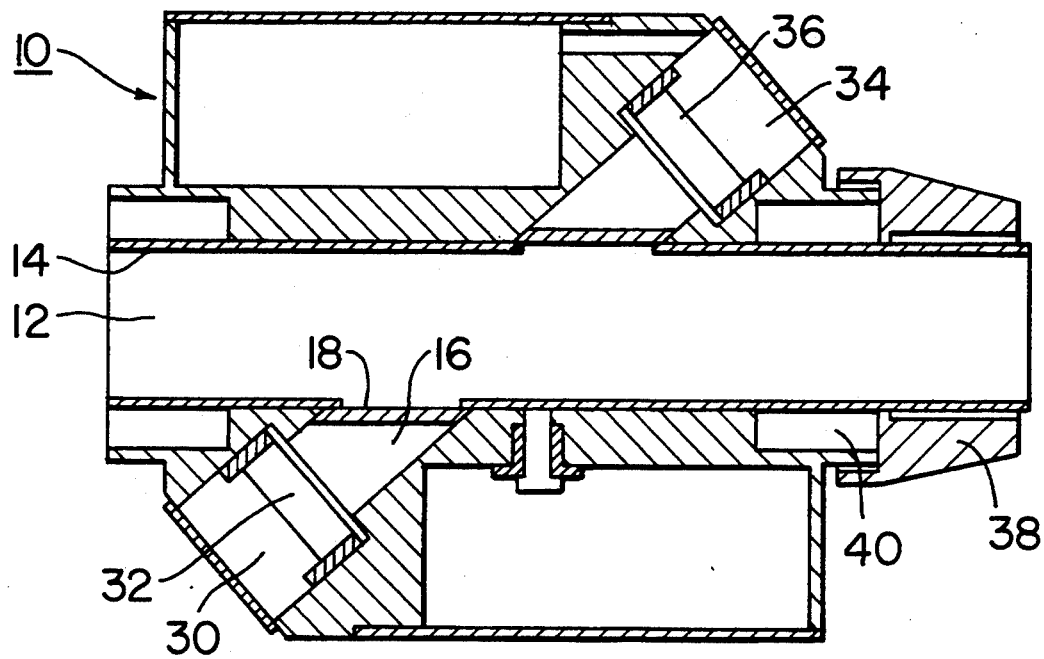
FIG. 1 is a sectional elevation of an ultrasonic spirometer in accordance with a first embodiment of the present invention.

The general structure of the ultrasonic spirometer 10 is essentially the same as that of the spirometer disclosed in the patent publication CH 669,463 A5. The central parts of this ultrasonic spirometer comprise the test duct 12 for the respiratory air and the test section 16 extending obliquely thereto. The transmitting and receiving elements 32 and 36 are arranged in separate chambers 30 and 36.

The test duct 12 has a sterile or possibly practically sterile duct 14 arranged arranged in it with an accurate fit, which at the transition to the test section 16 possesses test windows such that in suitable openings inerts 18 of foam rubber are arranged. These foam rubber inserts 18 are bonded at the edge to the walls of the respective opening in the test duct 12 and project into the respective obliquely extending lumen of the test section 16.

The substantially sterile duct 14 can consist of any suitable material. Thus for instance the invention contemplates the use of plastic tubes. It would be an advantage to utilize, for instance, a plastic which is readily biologically degradable. Basically, it would furthermore be possible to employ paper ducts or ducts of other sterilizable materials, which are readily biologically degradable.

The foam rubber inserts may be impregnated with a disinfectant.

The ultrasonic spirometer in accordance with FIG. 1 is divided in two in a fashion not illustrated in detail in the plane of the test duct 12. Accordingly it may be folded open for the insertion and removal of the sterile duct 14.

Figure 2A:
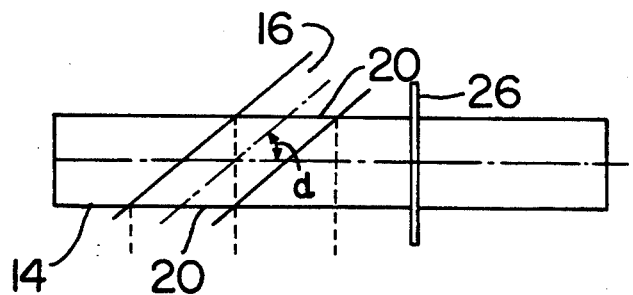
FIG. 2 shows a part of the ultrasonic spirometer in accordance with a second embodiment of the invention in two views.
Figure 2C:
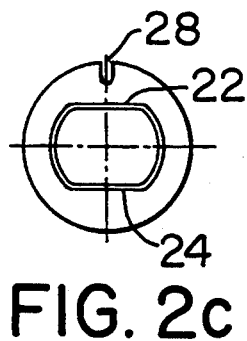
Figure 2B:
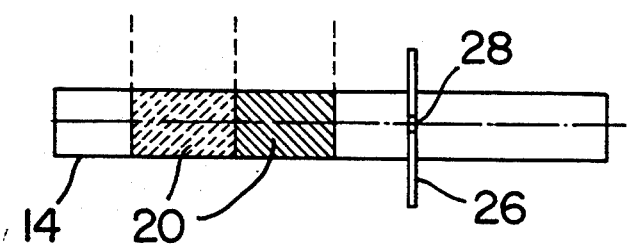

In the illustrated working embodiment of the invention of FIG. 2 the sterile duct 14 is, unlike the first embodiment of the invention made not with a circular cross section. As shown in the view of FIG. 2c, the sterile duct 14 has respectively two plane parallel lateral surfaces 22 and 24. It is to be seen from FIG. 2b that within these plane parallel plates 22 and 24 respective rectangular plates 20 are inserted for covering the test windows. These plates 20 extend in a co-planar manner to the parallel planes 22 and 24. A decisive point for the ability to function is that the plates 20 are so thin in comparison with the ultrasonic waves produced that they are able to be caused to vibrate by the ultrasonic wave so that the ultrasonic waves may be propagated as well past the window into the sterile duct 14. In the illustrated working embodiment of the invention the width of the rectangular plates 20 is also equal to the width of the plate surfaces 22 and 24 of the sterile duct 14.

In FIG. 2a the position of the test window 20 is indicated once again, the course of the test section 16 being indicated. It is set at a slope of α. The sterile test duct possesses a flange 26 with a locating recess 28. If the sterile duct 14 in accordance with the embodiment illustrated in FIG. 2 is set in an ultrasonic spirometer in accordance with FIG. 1, then owing to the design of the flange 26 this can take place in a simple fashion by unscrewing the flange 38 and the annular part 40 and, respectively, taken out and the sterile duct 14 may be inserted. The exact position of the sterile duct 14 in the test duct is ensured by a projection in the locating recess 28 on the flange 26 of the sterile duct 14.

The present invention constitutes an accurate spirometric sensor, which does not obstruct flow of breath and furthermore only involves a disposable part of minimum size which is also biologically degradable and which in use provides a hygienic guard.

I claim:

1. An ultrasonic spirometer, comprising a pair of cells, of which one is a transmitter cell and the other is a receiver cell, said cells are arranged in a test section with an oblique or perpendicular alignment to an axis of a duct containing a test section, wherein:
    a substantially sterile readily replace duct is placed with an accurate fit into the test duct, said readily replaced duct possessing at a transition to the test section a plurality of test windows wherein inserts are inserted in corresponding openings, said inserts being transparent to acoustic waves but substantially impermeable to microorganisms and dirt, wherein the substantially sterile duct has locating means for accurately fitting the same into the test duct.

2. The spirometer as claimed in claim 1, wherein said inserts consist of elastic plastic.

3. The spirometer as claimed in claim 2, wherein said inserts consist of foam rubber.

4. The spirometer as claimed in claim 1, wherein said inserts are impregnated with a disinfectant.

5. The spirometer as claimed in claim 1, wherein the test duct is divided so that by folding open the spirometer the duct which is substantially sterile, may be accurately inserted in the correct position therefor.

6. The spirometer as claimed in claim 1, wherein the inserts consist of plates, which in comparison with the wave lengths produced are so thin that they may be caused to vibrate by ultrasonic waves.

7. The spirometer as claimed in claim 6, wherein the substantially sterile duct possesses two oppositely placed surfaces whose width is the same as the width of the rectangular plates.

8. The spirometer as claimed in claim 6, wherein said plates consist of Mylar film.

9. The spirometer, wherein the substantially sterile duct possesses a flange 26 with a locating recess.

* * * * *